(12) United States Patent
Leason

(10) Patent No.: US 7,878,488 B1
(45) Date of Patent: Feb. 1, 2011

(54) METHOD AND DEVICE FOR VOLATIZING AROMATIC OILS IN RESPONSE TO WIRELESS SIGNALS

(76) Inventor: David Leason, 28 Garey Dr., Chappaqua, NY (US) 10514

( * ) Notice: Subject to any disclaimer, the term of this patent is extended or adjusted under 35 U.S.C. 154(b) by 939 days.

(21) Appl. No.: 11/745,444

(22) Filed: May 7, 2007

(51) Int. Cl.
*B01F 3/04* (2006.01)

(52) U.S. Cl. .......................... 261/26; 261/30; 261/142; 261/DIG. 89

(58) Field of Classification Search ............ 261/30, 261/100, 101, 142, DIG. 88, DIG. 89, 26, 261/27
See application file for complete search history.

(56) References Cited

U.S. PATENT DOCUMENTS

| | | | |
|---|---|---|---|
| 4,695,434 A * | 9/1987 | Spector ................. | 422/116 |
| 6,283,461 B1 * | 9/2001 | Joshi et al. ............ | 261/142 |
| 6,390,453 B1 | 5/2002 | Frederickson et al. | |
| 6,537,256 B2 | 3/2003 | Santini, Jr. et al. | |
| 6,581,915 B2 | 6/2003 | Bartsch et al. | |
| 6,783,084 B1 | 8/2004 | Nelson | |
| 2002/0030291 A1 * | 3/2002 | Joshi et al. ............ | 261/142 |
| 2005/0142508 A1 | 6/2005 | Lee et al. | |
| 2005/0201944 A1 | 9/2005 | Kvietok et al. | |
| 2006/0018803 A1 | 1/2006 | Kvietok et al. | |
| 2006/0067859 A1 | 3/2006 | Laudamiel-Pellet et al. | |
| 2006/0110281 A1 | 5/2006 | Smith | |
| 2006/0196100 A1 | 9/2006 | Laudamiel-Pellet et al. | |
| 2006/0261179 A1 | 11/2006 | Davies et al. | |
| 2007/0133206 A1 * | 6/2007 | Demarest et al. ........ | 362/253 |

* cited by examiner

*Primary Examiner*—Scott Bushey
(74) *Attorney, Agent, or Firm*—Leason Ellis LLP

(57) ABSTRACT

Volatization of oil to impart a scent into air in an environment includes sensing a wireless transmitted signal in the environment and selectively outputting a control signal in response to the sensed wireless signal. The control signal activates a heater. Oil is transferred to a target region proximate the heater. The oil is actively volatized by the heater. Optionally, further wireless signals can be ignored until a cycle is complete, such that volatization occurs in response to only a portion of wireless signals in the environment. An apparatus can be so constructed to volatize oil in response to wireless signal events in the environment.

19 Claims, 3 Drawing Sheets

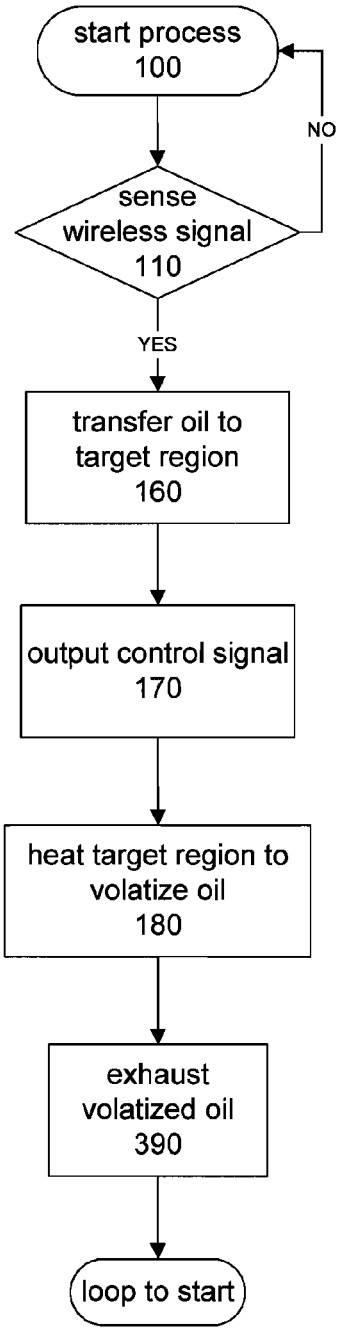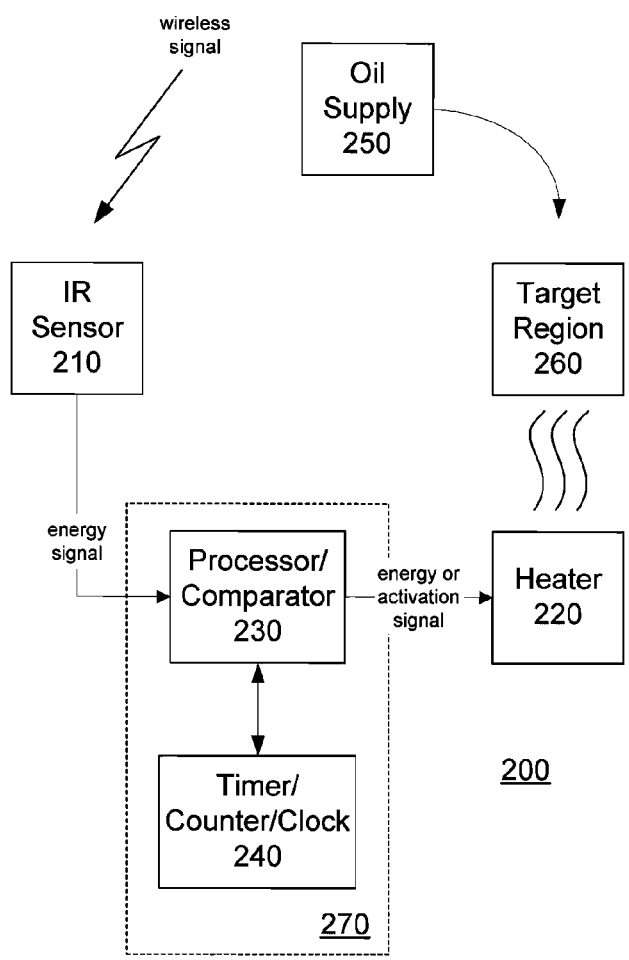
Figure 1
Figure 2

METHOD AND DEVICE FOR VOLATIZING AROMATIC OILS IN RESPONSE TO WIRELESS SIGNALS

FIELD OF THE INVENTION

The present invention relates to volatizers for aromatic oils and the like, and more particularly to a method and system that sense wireless signal events in an environment and respond to the presence of such signals with the volatization of an amount of oil or the like.

BACKGROUND OF THE INVENTION

Many consumer electronics operate in response to signals transmitted by remote controls. For example, televisions, stereos, radios, lights, cameras, and countless other devices are supplied with dedicated or universal remote controls that transmit coded signals. The coded signals are received, interpreted and used to change settings in such devices from a distance. Typically, the coded signals are transmitted in the infrared region of the electromagnetic spectrum, but sometimes they are transmitted at radiofrequency wavelengths. The coded signals can change the power on/off state, volume, channel, and myriad other settings.

Remote controls are beneficial because they allow persons to enjoy electronics without having to go to the device each time a change in setting is desired. These same persons might enjoy or appreciate watching television or listening to music, for example, while enjoying a favorite scent that permeates their environment from a volatized essential oil or the like.

However, quality scents produced by burning essential oils require effort beyond operating a remote control. Essential oils are typically burned under a flame and that requires votive candles, a burner, oil, a match and effort to initiate and supervise the volatization process.

On the other hand, some scents are available in forms that can perfuse the air continuously or intermittently with the assistance of heat/electricity in an automated way. On example include the gel- and oil-based products sold commercially as Glade Plugins®, available from S.C. Johnson and Company. Such household products have associated drawbacks, chief among them is that the scent is constant, and therefore becomes less noticeable. Though devices have been made that cycle through different scents, volatizers on the market today generally lack the refinement that an essential oil can provide, and universally fail to provide active control over when the volatizer is to operate in a subtle way that integrates with everyday modern life.

The present invention provides a new product category in the form of systems and methods that add wireless responsiveness to an electronic volatizer, and that automatically provide a scent in response to a wireless signal without regard to the encoded command in the signal itself. Such a system and method is advantageous over continuous or intermittent scent dispensers by emitting the scent only when persons are in the room or in the vicinity of the scent emitting device and engaging in an activity that includes the use of a remote control.

SUMMARY OF THE INVENTION

In accordance with one aspect of the invention, a method for volatizing oil and thereby imparting a scent to air in an environment is provided. The method includes sensing a wireless transmitted signal in the environment and selectively outputting a control signal in response to the sensed wireless signal. An oil is transferred to a target region, at least a portion of which is heated in response to the output control signal.

Methods in accordance with this aspect of the invention can include additional steps and refinements. For example, the passage of time since sensing the wireless transmitted signal can be measured, and the control signal can be issued only if a wireless signal is transmitted after the passage of a prescribed amount of time. In the meantime, any subsequent wireless signal can be ignored, such that no further control signals and hence no further active volatization of oil occurs until the prescribed amount of time has passed. Also, the transfer of oil to the target region can be made in response to the sensed wireless signal. Optionally, the volatized oil can be exhausted, actively or passively.

In accordance with another aspect of the invention, an apparatus for volatizing oil so as to impart a scent to air in an environment is described. The environment is one that includes a wireless signal from a remote control. The apparatus includes a housing which is configured to removably receive a container of oil. A heater within the housing is energized in response to an energy signal. A target region is disposed so as to support an amount of oil proximate to the heater. A sensor, supported by the housing, outputs the energy signal in response to the wireless signal in the environment. A variety of transfer mechanisms such as those described herein or later developed can be provided to transfer oil to the target region so that it is available for volatizing by the heater.

An apparatus constructed in accordance with this aspect of the invention can include additional components and functionality. For example, the apparatus can be a state machine having various states (cycle in progress, cycle complete) which change when at least one criterion is satisfied. Also, the mechanism employed to transfer oil to the target region can activate and make such transfers in response to energy signals from the sensor.

These and other aspects, features and advantages shall be apparent from the accompanying drawing figures and detailed description of certain embodiments of the invention.

BRIEF DESCRIPTION OF THE DRAWING FIGURES

FIG. 1 is a flow chart diagram of a process for volatizing oil in response to a wireless signal event in accordance with an embodiment of the invention;

FIG. 2 is a functional block diagram which illustrates basic components that operate to volatize oil in response to a wireless signal event in accordance with an embodiment of the invention;

DETAILED DESCRIPTION OF CERTAIN EMBODIMENTS

Figure 3:
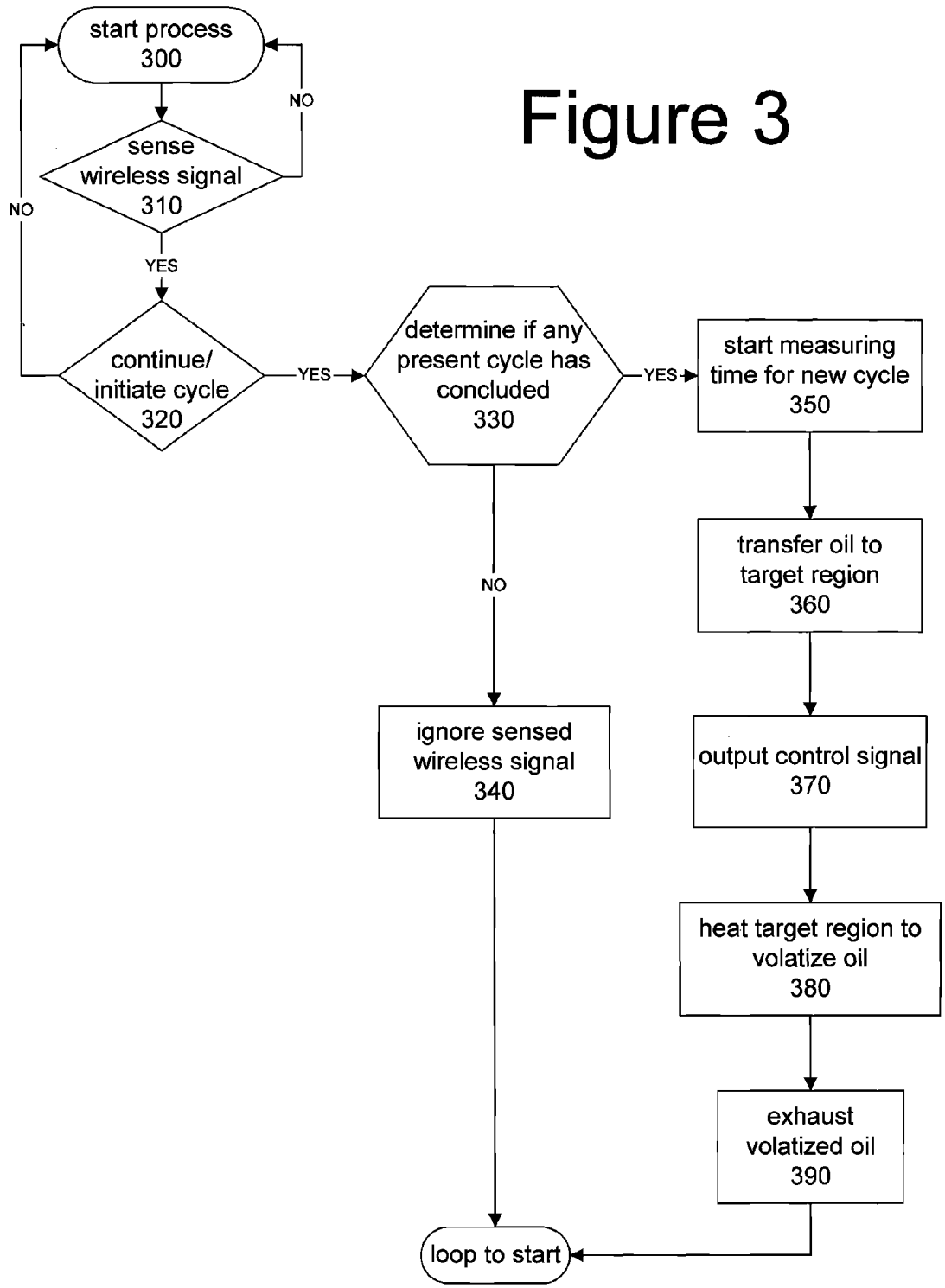
FIG. 3 is a flow chart diagram of the process of FIG. 1, showing additional blocks in accordance with a further aspect of the invention that can be performed.

By way of overview and introduction, the invention concerns a system and method that actively respond to wireless events with an aromatic scent. When wireless signals are present in an environment that includes a machine constructed in accordance with the invention, aromatic oil is caused to volatize. As a result, the environment is enhanced by exhausting the aromatic scent into the environment in response to the wireless signal(s).

Referring now to FIG. 1, a device responsive to a wireless signal can operate as outlined in process 100. A wireless signal is sensed at block 110, such as in response to a press of a button on a remote control. The wireless signal can comprise an infrared signal, a radio frequency signal, or an optical signal and can encode any of a variety of commands such as power on, volume up, lights off, screen down, pause, play, and so on. The wireless signal detection is ambivalent to the encoded command within the signal itself. All that is sensed is the presence of energy in the relevant signal band (e.g., in the IR signal band). The wireless signal causes an energy signal to be output in response to the wireless signal detection. Conventional IR, RF and optical detectors are suitable for this purpose. For example, a phototransistor detector is available from RadioShack Corporation as Model 276-142.

At block 160, a dose of a volatile oil is transferred to a target region for volatization. The target region can be a surface of any of a variety of shapes, but a generally bowl-shape is particularly suitable for receiving and holding the oil. In one implementation, the oil is transferred from a container in response to sensing the wireless signal at block 110. In another implementation, the oil is transferred from a container at a periodic interval, such as every 15 minutes after the device is turned on. In another implementation, transfer to a target region is by opening an oil container having a well which already holds one to a few drops of oil within the well and positioning the well proximate to the heater. The well can have a conductive exterior surface that completes a circuit when contacted by a resistance soldering tool in order to effect heating and volatization of the oil.

The oil container itself can have any of a variety of forms, including a conventional bottle. The container should have an outlet suitable for transferring a small dose of oil, such as a film on a target surface to be heated or droplets. The container, its lid, or an attachment to the container (e.g., a screw-on attachment) can include a plunger or a squeezable component that compresses to transfer the oil to be volatized to the target region. Compression can be by energizing a solenoid against the squeezable component or plunger. The container can have a mouth that opens to permit a dip stick to be immersed, withdrawn and thereafter used to transfer oil drops from the container to a target region. The container can have a spray-pump head that transfers a mist of droplets to the target region, such as in response to a solenoid depressing the spray pump head. The container itself can include a target region from which oil is volatized. For instance, oil can be held in plural wells, each holding one to a few drops, with delivery to the target region comprising opening a well and transferring the well to a position proximate to the heater so that volatization into the environment can occur. In this last variation, the oil is not transferred from one container to a separate target region, but the oil and its container together are transferred into proximity or contact with the heater from a spaced resting location.

At block 170, an energy signal is output by the detector in response to detecting a wireless signal within its detection band, and the energy signal causes a dose supported in the target region to be actively volatized. When a wireless signal is sensed, an output of the wireless signal detector changes state. For example, if the detector is a phototransistor, a detected signal can forward bias the transistor and cause it to go from a non-conductive state to a conductive state. The phototransistor can be connected to a circuit in several ways, but no matter how it is connected its change in state produces an energy signal that, with or without amplification, triggers a heater circuit to turn on.

The energy signal activates a heater circuit including a heater positioned so as to raise the temperature of the target region, as indicated at block 180, thereby increasing the rate of oil volatization. The heater portion of the heater circuit can comprise a variety of sources, but preferably is comprised of a device that rapidly heats and thereafter rapidly cools so that volatization follows a step-function like curve. One suitable source is the resistance soldering tool available from Hyperion Innovations Inc., d/b/a ColdHeat, Bellevue, Wash. A resistance soldering tool generates substantial heat when its spaced prongs are brought into contact with a conductive surface. By forming the target region as a conductive bowl or housing, a heater circuit can drive a solenoid which moves the resistance soldering tool into brief contact with the conductive target surface to heat it, and then separates the target surface from the resistance soldering tool tip so that both the tool and the target surface cool promptly. Alternatively, the heater circuit can comprise a switch that applies power to and thereafter separates the power from the resistance soldering tool tip, the tip being in continuous contact with a conductive target surface. Other sources for heat have longer warm-up and cool-down cycles, but can be used in heater circuits, including filament-based heaters made of tungsten and tungsten alloys and other materials conventionally used in electric toasters, space heaters, and the like.

At block 190, the volatized oil exhausts from the device. The oil can exhaust passively through a vent in the cabinet of the device, or the exhaust can be assisted by a fan or blower.

FIG. 2 schematically illustrates a device 200 that can implement the blocks of process 100. The device 200 includes a sensor 210, illustratively an IR sensor such as is commercially available from a wide variety of vendors. The sensor 210 senses wireless signals within the environment in which the device 200 is situated and outputs an energy signal whenever a wireless signal is detected. The wireless signal need only be within a selected band of the electromagnetic spectrum to be sensed. The content of the signal itself (i.e., its payload) is irrelevant to the device 200; however, it is typically transmitted in order to control or influence another device in or operative within the environment (e.g., a television or stereo system).

The energy signal can be used to actuate a heater 220, though the energy signal output by the sensor may require amplification or other circuitry to latch the wireless event and cause the heater to be driven in the on state for an appropriate period of time to volatize the oil in the target region. In more sophisticated devices constructed in accordance with further aspects of the invention, the energy signal can be processed by state circuitry 270. The state circuitry can comprise analysis circuitry 230 such as a processor, comparator or other logic circuitry and time measuring circuitry 240 such as a clock, timer or counter. The analysis circuitry 230 can selectively respond to the energy signal by (1) producing an activation signal that in turn energizes the heater 220 under certain conditions and for a desired minimum amount of time and (2) producing no activation signal in response to the energy signal under other conditions. The time measuring circuitry 240 can provide the analysis circuitry 230 with data useful in determining when and whether to issue the activation signal and can be part of the analysis circuitry itself.

Meanwhile, a dose of oil from a supply 250 such as a bottle, cartridge or well is transferred or delivered to a target region (or surface) 260. The dose can be a metered or variable amount of oil. Preferably, an aliquot of oil is delivered to the target region 260 so that a controlled amount of heating can volatize the aliquot of oil in a predictable and automated manner. In this regard, the heater 220 preferably comprises a heating element that can rapidly achieve a temperature sufficient to volatize oil on the target surface. To "volatize" oil, as used in this disclosure document, the temperature of the target surface is actively raised to a higher temperature than that of the ambient, but not necessarily to any particular temperature. The heater can be, for example, a resistance soldering tool such as popularized in the ColdHeat soldering iron which can achieve a temperature suitable for heating a conductive target in around one second.

Referring now to FIG. 3, process 300 includes further blocks that can be implemented in response to a wireless signal event in the environment. As in process 100, a wireless signal is sensed at block 310 by a sensor 210. Once a wireless signal has been sensed, a cycle can be initiated or continued, as indicated at block 320, depending on the criterion being used to start the cycle. A "cycle" is started in accordance with an established criterion and continues for a period of measured time that ends a present interval. The criterion for commencing a cycle can vary widely with different implementations of the invention, and several paradigms are described below by way of example. In comparison, an "interval" includes a cycle plus the time before the cycle begins (during which the paradigm for volatizing oil has not been satisfied).

At either block 320 or block 330, (1) a cycle is started in response to certain wireless signal events that now satisfy the paradigm, or (2) a previously started cycle continues, or (3) a paradigm has not been satisfied and so the process loops back to sense further wireless signals. A basic paradigm tests for a single wireless signal which is used to initiate a cycle, either after power-up of the device 200 or at the conclusion of a present cycle, both of which can be determined at block 330. The determination at block 330 is made with regard to state circuitry 270, which can include the analysis circuitry 230 and the time-measuring circuitry 240 described above. Thus, the signal sensed at block 310 can be assessed as being the beginning of a first interval after power-up based on programmed or wired logic of the state circuitry 270. Similarly, the sensed signal can be determined as having occurred during a present cycle (concluded?: NO) or after a present cycle has concluded (concluded?: YES) with reference to the present values in the time measuring circuitry 240. The sensed signal also might be determined as not completing the requirements of the paradigm to cause volatization, resulting in a loop back to the start of process 300. The time measuring circuitry can comprise a timer that increments or decrements, a clock that runs freely or runs after an impulse, or a counter. Each of these digital elements can be gauged against a reference or stored value to determine how much time has elapsed since the start of a cycle, as understood by persons of ordinary skill in the art.

If the present cycle has not concluded, then the wireless signal event sensed at block 310 can be ignored, as indicated at block 340 in the "concluded?: NO" branch of the decision tree. This is desirable when actuation of the heater and volatizing the dose is intended to be responsive to a portion, but not all, of the wireless signal events in the environment. If the wireless signal is ignored, the process flows back to block 310 to sense a next wireless signal.

On the other hand, a cycle can be commenced when an assessment of the present value of the time measuring circuitry 240 indicates that there is no active cycle in the present interval. In that case, assuming that the paradigm has been satisfied, the process flow proceeds along the "concluded?: YES" branch of the decision tree to implement blocks 350 through 390. At the conclusion of the cycle, the interval ends and subsequent wireless events that satisfy the paradigm will be analyzed at block 330, as already described.

At block 350, time starts being measured for a new cycle using any of a variety of devices. For instance, time can be measured using a clock by noting a clock value at one part of the cycle, e.g., upon reaching block 350, and computing passage of time with reference to updated clock values as the clock continues to run. Likewise, time can be measured by monitoring changes in the count value of a counter. The values updated by the counter are indicative of the passage of time and hence can be used at block 350 as a measurement of time.

Figure 4:
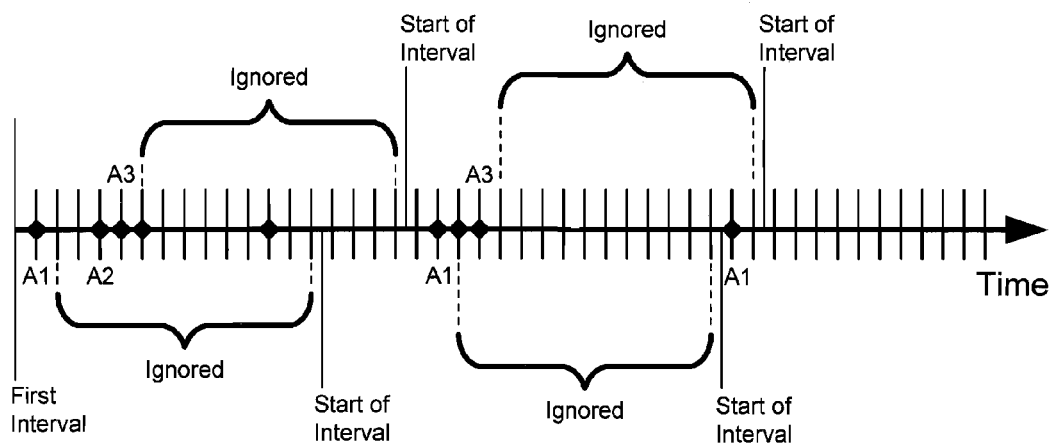
FIG. 4 is an exemplary timing diagram that illustrates two possible operations of a device in accordance with the flow diagram of FIG. 3.

Blocks 360, 370, 380, and 390 are functionally the same as blocks 160, 170, 180, and 190, respectively, and are not described further except in relation to FIG. 4.

FIG. 4 is a timing diagram that illustrates two examples of the state circuitry 270 that can be employed in the process 300 of FIG. 3. In FIG. 4, three intervals are shown along a time line in which each "tick" can represent any quantity of time. For purposes of discussion only, each tick represents the passage of one minute of time. Within any given interval, a cycle can be commenced which includes a volatization step and a window in which further wireless signals are ignored, by satisfying the test at blocks 320 and 330. FIG. 4 illustrates how a cycle can be initiated in response to certain wireless signal events sensed at block 310, while ignoring others.

One paradigm for initiating a volatization cycle is depicted by the markings below the time axis in FIG. 4. This paradigm requires only one wireless signal event to trigger the start of a cycle. "A1" indicates a wireless signal having been detected. After detection of the wireless signal, a cycle proceeds by satisfying the determination at block 330. The "A1" close to the left side of FIG. 4 is the commencement of a first cycle. Time is then measured at block 350. A dose is transferred to the target surface at block 360. The heater is energized by the energy signal output at block 370 to volatize the dose at block 380. The volatized dose exhausts into the environment at block 390. The process loops back to start until a subsequent wireless signal is detected. Upon detection of the next wireless signal event, "A2," that event undergoes analysis at block 330 and in this example is determined to be within a cycle that has not yet concluded. As a result, the signal A2 is ignored at block 340. Subsequent signals are also ignored until the measuring time has reached a specified criterion (for example, a count value, a time value, a time differential value, etc.). Thereafter, a new cycle can be initiated in which a next wireless signal event sensed at block 310 will be analyzed at block 330 as having arrived after the conclusion of a present cycle. Such an event will be in a next interval and will cause oil volatization as described above and will start the measurement of time in the new cycle. More generally, any wireless signal events that are sensed before the end of a present cycle are ignored until the start of a new interval, and so on.

Another paradigm for initiating a volatization cycle is depicted by the markings above the time axis in FIG. 4. This paradigm requires three wireless signal events before a cycle is triggered. Under this paradigm, the analysis circuitry 230 keeps track of the number of wireless signal events that have been detected for purposes of determining when to volatize oil and start a cycle that will prevent any further volatizations until the present cycle (and interval) terminates. Only after the analysis circuitry concludes that the paradigm has been satisfied does a cycle begin and time starts to be measured. Thus, at block 320, a cycle is only initiated if the paradigm is satisfied. In the example above the time line in FIG. 4, that requires three wireless signal events.

"A3" indicates a wireless signal event having been sensed and identified as the third wireless signal. In the time line of FIG. 4, the first interval after power-up has wireless signals A1-A3 spaced in time, such that the first occurs about a minute after power up while the second and third wireless signal events occur at 4 and 5 minutes after power up (scale: 1 tick=1 minute), respectively. Once the third wireless signal has been identified, according to this paradigm, a cycle can proceed precisely as described above. In other words, because a cycle has been initiated at block 320, the decision block 330 will be satisfied, time will begin being measured at block 350, a dose will be transferred to the target surface at block 360, the heater will be energized by the control signal output at block 370, the dose will be volatized at block 380, and the volatized dose will exhaust into the environment at block 390. Wireless signal events during the present cycle are ignored, and wireless signal events after the conclusion of the cycle (and interval) are sensed and counted until the paradigm ($3^{rd}$ wireless signal) is again satisfied.

Figure 5:
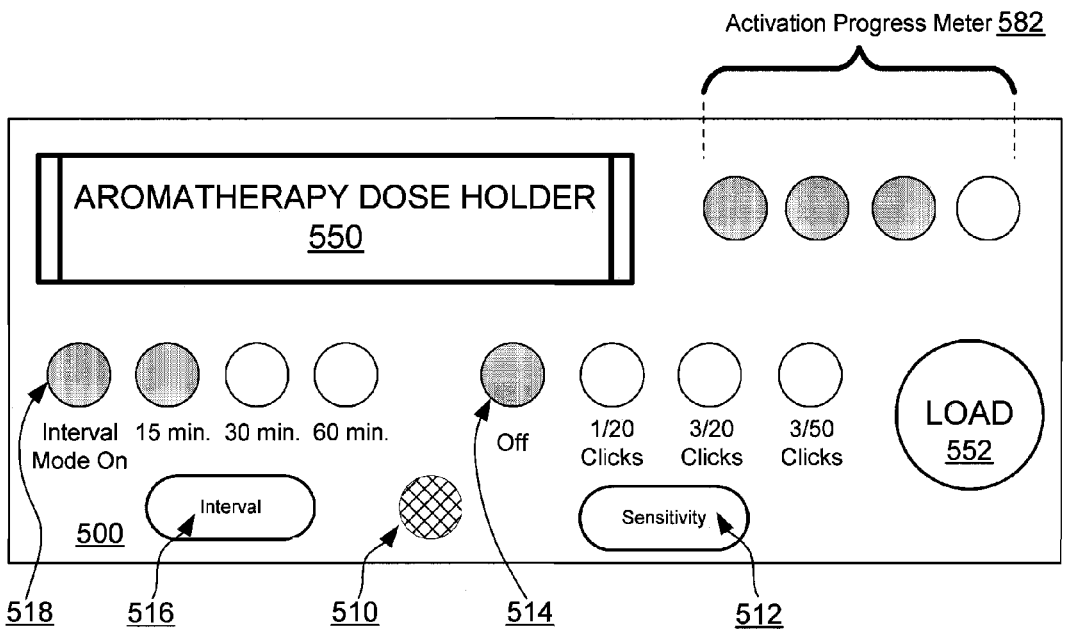
FIG. 5 is a conceptual diagram of an exemplary device constructed to volatize oil in response to a wireless signal event.

FIG. 5 is a conceptual illustration of a device 500 that can implement one or more aspects of the invention, including some or all of the blocks depicted in FIGS. 1 and 3. The device 500 includes a wireless signal sensor 510 which can be the same type of device as sensor 210. The device has selectable sensitivity through a control 512 which can take the form of a press-button, for example. The control 512 can cycle through different states, or multiple controls 512 can be provided to change the sensitivity of the device to any of a number of pre-configured or user-configurable wireless-signal event paradigms. For example, the paradigm of a 1-click remote-control response can be selected, or the paradigm of a 3-click response can be selected, or a hybrid paradigm can vary in sensitivity over time in response to a program executing in the analysis circuitry 230 or in response to data gathered dynamically based on the user's remote-control usage in the environment. The sensitivity settings can also gauge the passage of time in the form of a count of wireless signal events, such that 1-click can start an interval and the interval can continue (and ignore subsequent clicks) until, say, a $20^{th}$ click is sensed. In this way, a user who actively presses remote-control keys can control the rate of volatization in relation to his or her clicking habits. As noted, the device 500 can respond to wireless signal patterns of the user to dynamically set a trigger rate. The setting can be with regard to the size of the environment, which can be indicated to the device 500 by another control or dipswitches (not shown). An indicator 514 displays the status of the sensitivity setting, including an "off" status.

Device 500 can also have an interval control 516, as shown, which can be constructed the same way as control 512. The interval control can be provided if the user is to be given a choice of operating modes. If the interval mode is "on," as indicated by lamp 518, it is in one of several settings (e.g., every 15 minutes, as shown in FIG. 5) that define the frequency of volatization. The interval mode can proceed without regard to whether there are any wireless signal events. This mode of operation can be provided, if desired, but is less preferred because it is not responsive to events within the environment.

Oil is loaded into a dose holder 550 that can be accessible from a front panel of the device 500, as shown. The dose holder can hold one or a variety of oils at the same time. For example, oil can be provided in wells of a single tray that is housed in the dose holder 550. The tray can have a top that can slide or be punctured to expose each well. The wells can each hold the same oil or can hold different oils so as to impart variety to the volatized scents. Also, the dose holder can seat bottles and containers of a prescribed shape and construction, such as one or more bottles of essential oils. The dose holder can be opened and closed using a control 552, in a manner analogous to an optical-disc loading-tray for loading oil containers into the device. The dose holder can be a manually loadable access point which enables other portions of the device 500 to transfer oil from that location to the target region or surface.

As wireless signal events are detected, progress toward a next activation of the heater to volatize oil can be indicated, if desired. An activation progress meter 582 can include multiple lamps that are illuminated or one or more lamps that change in intensity as the next activation draws near. If the interval mode is selected at 15 minute intervals, then the activation meter 582 of FIG. 5 could indicate that approximately 11 minutes have gone by since the last activation. Similarly, if a 1-click-in-20 paradigm is selected, then three out of four illuminated lamps in the activation progress meter would indicate that the heater will activate in approximately 6 more clicks.

The settings of device 500 can be changed by remote control, and an option can be that any encoded wireless signal that is to direct the modes and operation of the device 500 itself can be identified and isolated so as to not initiate a cycle or otherwise cause volatization of an oil, in and of itself.

The invention has been described with regard to certain embodiments thereof to aid in an understanding thereof, but the invention itself is more broadly defined by the recitations in the claims appended hereto, and equivalents of such recitations, and the claims are to be read with that in mind.

I claim:

1. An apparatus for volatizing oil and thereby imparting a scent to air in an environment that includes a wireless signal from a remote control that is within a selected band of the electromagnetic spectrum, comprising:
    a housing configured to removably receive a container of oil;
    a heater within the housing that is energized in response to an energy signal;
    a target region disposed so as to support an amount of oil proximate to the heater;
    a sensor supported by the housing and outputting the energy signal in response to detection of a presence of energy within the selected band of the electromagnetic spectrum due to the wireless signal in the environment and without regard to an encoded command in the wireless signal itself; and
    means for transferring the amount of oil to the target region;
    whereby the transferred oil is actively volatized by the heater at a time after the occurrence of the wireless signal in the environment.

2. The apparatus of claim 1, further comprising means for controlling a state of the device so as to activate the heater when at least one criterion is satisfied.

3. The apparatus of claim 1, wherein the transferring means transfers the amount of oil in response to the sensor outputting the energy signal.

4. The apparatus of claim 1, further comprising state circuitry operative to be responsive to at least a portion of the wireless signals in the environment.

5. The apparatus of claim 1, further comprising state circuitry operative to measure a passage of time after the energy signal is output, and wherein the state circuitry is configured to preclude active volatization of oil immediately after the occurrence of one or more further wireless signals in the environment that occur prior to the passage of a prescribed amount of time.

6. The apparatus of claim 1, further comprising means for exhausting any oil that has been volatilized away from the target region.

7. The apparatus of claim 1, wherein the sensor outputs the energy signal in response to an infrared wireless signal in the environment.

8. The apparatus of claim 1, wherein the target region is a target surface and wherein the oil transferring means transfers oil from the container to the target surface.

9. The apparatus of claim 1, wherein the target region is a target surface and wherein the heater comprises a resistance soldering tool.

10. The apparatus of claim 1, wherein the sensor supported by the housing is configured to selectively output the energy signal in response to the wireless signal in the environment.

11. The apparatus of claim 1, further comprising:
circuitry operatively coupled to the sensor; and
a latch circuit in communication with the circuitry and operable to cause the heater to be energized in an on-state for a period of time.

12. An apparatus for volatizing oil and thereby imparting a scent to air in an environment that includes a wireless signal from a remote control that is within a selected band of the electromagnetic spectrum, comprising:
a housing configured to removably receive a container of oil;
a heater within the housing that is energized in response to an activation signal;
a target region disposed so as to support an amount of oil proximate to the heater;
a sensor supported by the housing and outputting an energy signal in response to detection of a presence of energy within the selected band of the electromagnetic spectrum due to the wireless signal in the environment and without regard to an encoded command in the wireless signal itself;
state circuitry arranged to respond to the energy signal by producing the activation signal under certain conditions; and
means for transferring the amount of oil to the target region;
whereby the transferred oil is actively volatized by the heater at a time after the occurrence of the wireless signal in the environment.

13. The apparatus of claim 12, wherein the state circuitry comprises time measuring circuitry configured to measure a passage of time after the energy signal is output, and wherein the state circuitry is configured to preclude the production of the activation signal after the detection of one or more further wireless signals in the environment that occur prior to the passage of a prescribed amount of time.

14. The apparatus of claim 12, further comprising a sensitivity control on the housing and operable to cause the activation signal to energize the heater only after a prescribed number of wireless signal events have been detected, each wireless signal event comprising the detection of the wireless signal in the environment.

15. The apparatus of claim 12, further comprising means for exhausting any oil that has been volatilized away from the target region.

16. The apparatus of claim 12, wherein the sensor outputs the energy signal in response to an infrared wireless signal in the environment.

17. The apparatus of claim 12, wherein the target region is a target surface and wherein the oil transferring means transfers oil from the container to the target surface.

18. The apparatus of claim 12, wherein the target region is a target surface and wherein the heater comprises a resistance soldering tool.

19. The apparatus of claim 12, further comprising a latch circuit connected so as to cause the heater to remain energized for a period of time.

* * * * *